US012667496B2

(12) United States Patent
Pang et al.

(10) Patent No.: US 12,667,496 B2
(45) Date of Patent: Jun. 30, 2026

(54) VIBRATION-RESISTANT DRY SKIN ADHESIVE PATCH

(71) Applicant: RESEARCH & BUSINESS FOUNDATION SUNGKYUNKWAN UNIVERSITY, Suwon-si (KR)

(72) Inventors: Changhyun Pang, Suwon-si (KR); Da Wan Kim, Suwon-si (KR); Jinhyung Kim, Suwon-si (KR)

(73) Assignee: RESEARCH & BUSINESS FOUNDATION SUNGKYUNKWAN UNIVERSITY, Suwon-si (KR)

( * ) Notice: Subject to any disclaimer, the term of this patent is extended or adjusted under 35 U.S.C. 154(b) by 184 days.

(21) Appl. No.: 18/407,644

(22) Filed: Jan. 9, 2024

(65) Prior Publication Data

US 2024/0307232 A1     Sep. 19, 2024

(30) Foreign Application Priority Data

Jan. 11, 2023     (KR) .......................... 10-2023-0003804

(51) Int. Cl.
    *A61F 13/02*     (2024.01)
    *A61F 13/0246*     (2024.01)
    *A61F 13/00*     (2006.01)

(52) U.S. Cl.
    CPC ...... *A61F 13/0253* (2013.01); *A61F 13/0243* (2013.01); *A61F 2013/00131* (2013.01)

(58) Field of Classification Search
    CPC ...... G06F 3/016; G06F 3/014; A61F 13/0243; A61F 13/0253

USPC ............................................................. 156/1
See application file for complete search history.

(56) References Cited

U.S. PATENT DOCUMENTS

| | | | | |
|---|---|---|---|---|
| 2016/0037885 A1* | 2/2016 | Vito | ..................... | A43B 23/028 |
| | | | | 224/191 |
| 2020/0163844 A1* | 5/2020 | Pang | ...................... | A61K 8/733 |
| 2022/0300076 A1* | 9/2022 | Casset | ..................... | G06F 3/041 |

OTHER PUBLICATIONS

Krajnak, K., "Health effects associated with occupational exposure to hand-arm or whole body vibration", J Toxicol Environ Health B Crit Rev. 2018 ; 21(5): pp. 1-17, Mar. 13, 2019. (Year: 2019).*

* cited by examiner

*Primary Examiner* — Abbas Rashid
*Assistant Examiner* — Gregory C. Grosso
(74) *Attorney, Agent, or Firm* — LEX IP MEISTER, PLLC

(57) ABSTRACT

The present invention relates to a dry adhesive patch including a first layer flexible and having a structure with embossed or engraved structures on one surface, a second layer flexible and comprising an interlocking coupling surface formed to engage with the embossed or engraved structures of the first layer, and a microchannel structure layer stacked on the opposite surface of the interlocking coupling surface, wherein the microchannel structure layer comprises an adhesive surface comprising a plurality of embossed portions having a flat surface and microchannel grooves between the embossed portions and is exposed.

22 Claims, 12 Drawing Sheets

FIG. 1

Frog-snail mimetic structure adhesive patch

Pigskin replica surface with sweat

Vibration generation

Vibration-resistant dry skin adhesive patch

Commercial hand tracking sensor module
[leap Motion Controller, Ultraleap Corp]

VIBRATION-RESISTANT DRY SKIN ADHESIVE PATCH

CROSS REFERENCE TO RELATED APPLICATION

The present application claims priority to Korean Patent Application No. 10-2023-0003804, filed on Jan. 11, 2023, the entire contents of which is incorporated herein for all purposes by this reference.

BACKGROUND OF THE INVENTION

Field of the Invention

The present invention relates to a vibration-resistant dry skin adhesive patch including a skin surface adhesive portion mimicking the microchannel structure of frogs, a microstructure connection portion mimicking the interlocking structure of snails, and a vibration transmission portion, to achieve high adhesive strength on wet and rough skin surfaces and maintain adhesion in vibrating environments.

Description of the Related Art

In more detail, the skin surface adhesive portion regulates the moisture on the adhesive surface by allowing the passage of moisture, such as sweat, generated on the skin through the channel structure for discharge, preventing continuous detachment and ensuring strong adhesive strength. The microstructure connection portion, when composed of interconnected elastic structures consisting of two or more layers, induces high adhesive strength and provides resistance to vibrations by dispersing surface stress. The vibration transmission portion facilitates transmitting vibrations to the human skin, allowing the vibration-resistant dry skin adhesive patch to have a high vibration transmissibility due to the preceding two structure layers.

The technology of skin adhesive patches, capable of adhering to and detaching from human skin, has emerged as a key technology in promising fields such as wearable devices, virtual reality/augmented reality (VR/AR) information transmission devices, and medical diagnostic patches for bio-information, along with recent advancements in electronic components and information communication technologies. In particular, these technologies are used in various forms, not only as sensors that read human movement or bio-information, but also as devices that attach to human skin and transmit tactile sensation through vibration devices. In this regard, the adhesive technology connecting devices with the human body is crucial. Such bioadhesive technologies have been broadly categorized into chemical adhesives employing chemical bonds and dry adhesives utilizing physical interactions such as van der Waals forces and capillary forces. Commercialized bioadhesive patches typically use acrylic-based chemical adhesives, which are inexpensive but have strong adhesion.

However, these chemical adhesives have various limitations. Typical chemical adhesives, such as glue and paste, can be irreversible, and pollutants from chemical adhesives can remain on the biological surface and cause irritation and inflammation. Moreover, in the case of bioadhesive patches used in devices for transmitting various information through physical stimuli such as vibrations, there is a limitation where the adhesive strength cannot be maintained if the chemical bond is repeatedly disrupted by vibrations.

Therefore, chemical adhesives have clear limitations when applied to bioadhesive patches utilizing electronic components, prompting growing attention towards bioadhesive patch technologies employing dry adhesives as an alternative. Dry adhesives, utilizing physical interactions to induce adhesion between two surfaces, are less likely to cause irreversible contamination or damage to the surface. Therefore, over the past decade, various dry adhesive technologies have been introduced and developed. For example, various adhesion methods exist in nature, such as the joining of insect wings, the feet of lizards, the tendrils of corn, the suction cups of octopuses, and the footpads of frogs. These natural adhesion systems have been mimicked to develop a wide range of adhesives, including medical bands, adhesive tapes, Post-it notes, Velcro, and many others, in a highly efficient manner. However, most dry adhesive systems are limited to dry surface environments, posing a challenge as they are unable to adhere in environments containing moisture such as sweat, blood, or exudate. Recently, various studies have attempted to achieve efficient adhesion in moist surface environments; however, there is still insufficient technological development, as stable adhesion in environments with continuous vibration and the inability to efficiently expel excess moisture make it challenging to ensure breathability of the adhesive surface. Additionally, adhesive structures designed for vibration resistance often face the challenge of low adhesion on wet surfaces due to sweat. Therefore, there has been a strong demand for the development of dry adhesive patches that can achieve dryness, moisture resistance, vibration resistance, and breathability.

SUMMARY OF THE INVENTION

The first object of the present invention is to provide a new skin adhesive patch that combines heterogeneous biomimetic microstructures to achieve vibration resistance and high adhesion on both dry and wet skin surfaces and a high vibration transmissibility. Specifically, by enhancing surface adhesion in a humid environment through a micro-adhesive structure connected to a microchannel structure with drainage properties and an interlocking structure maintaining high adhesion even under repetitive vibrations, the skin adhesive patch provides a mutually complementary solution that retains the inherent vibration resistance of snail leg muscle mimetic microstructures even in humid conditions.

The second object of the present invention is to develop electronic device interface technology applying the above-described biomimetic skin adhesive patch. The skin adhesive patch of the present invention, which has strong vibration resistance with microstructures internally connected in an interlocking structure, can be combined with electronic components that transmit and receive various information using physical stimuli. In addition, the skin adhesive patch of the present invention, which is robust in humid environments without losing its adhesive performance even with repeated use in application fields such as wearable devices that are mainly used in skin environments where a large amount of sweat is discharged due to exercise, enables innovative design and manufacturing methods previously unexplored.

The present invention provides a dry adhesive patch including a first layer flexible and having a structure with embossed or engraved structures on one surface, a second layer flexible and comprising an interlocking coupling surface formed to engage with the embossed or engraved structures of the first layer, and a microchannel structure layer stacked on the opposite surface of the interlocking coupling surface, wherein the microchannel structure layer comprises an adhesive surface comprising a plurality of embossed portions having a flat surface and microchannel grooves between the embossed portions and is exposed.

The interlocking coupling refers to a connection resulting from the engagement and entanglement of structures formed on the surfaces of the two layers. This means that there is engagement and entanglement of structures between the first and second layers. The actual adhesive surface is the surface where the exposed surface of the microchannel structure layer adheres to an adherend surface such as skin.

The patch of the present invention is a vibration-resistant patch. Vibration resistance refers to the property of maintaining adhesive strength even under vibration. In the present invention, vibration includes vibrations applied to the adherend surface, encompassing vibrations from the external environment of the adherend surface, as well as vibrations applied to the adhesive patch.

In the present invention, the vibration refers to a high-frequency vibration applied to the adhesive patch, e.g., vibration equal to or higher than 30 Hz.

In particular, the patch of the present invention provides high adhesion even on the moist surface of the skin.

The microchannel structure layer is stacked on the opposite side of the interlocking coupling surface of the second layer.

The second layer includes an embossed structure, and the first layer includes an engraved structure interlocking with the embossed structure.

The first layer and the second layer have different deformation rates in response to stress.

The second layer has a higher deformation rate in response to stress compared to the first layer.

The second layer is made of a more flexible material compared to the first layer.

The embossed portions of the microchannel structure layer are hexagonal in plane and form hexagonal columns.

The microchannel grooves have a width configured to allow capillary action by moisture between the adhered surface of the adhesive patch and the microchannels.

The width of the microchannel grooves ranges from 1 nm to 1000 μm.

The patch further includes a hydrogel layer on at least part of a base surface of the microchannel grooves.

The hydrogel layer has a height lower than the height of the embossed portions from the base surface of the microchannel grooves.

The microchannel structure layer includes at least one of natural rubber, nitrile rubber, acrylonitrile-butadiene rubber, styrene-butadiene rubber, chloroprene rubber, butyl rubber, isoprene-isobutylene rubber, ethylene propylene rubber, chlorosulphonated polyethylene rubber, acrylic rubber, fluoro rubber, polysulfide rubber, silicone rubber, butadiene rubber, isoprene rubber, urethane rubber, polyurethane, polyolefin thermoplastic elastomer (TPE), polystyrene TPE, polyvinyl chloride TPE, polyester TPE, polyurethane TPE, polyamide TPE, polyethylene terephthalate (PET), polydimethylsiloxane (PDMS), polyurethane acrylate, polyethylene naphthalate (PEN), and mixtures thereof.

The vibration is equal to or higher than 30 Hz.

The dry adhesive patch has a vibration transmissibility equal to or greater than 99%.

The interlocking coupling surface further comprises chemical adhesive.

The embossed or engraved structures have a diameter of 1 μm to 102 μm.

The first and the second layers are made of elastomeric or viscoelastic solid or viscoelastic fluid.

The first and second layers are made of at least one selected from the group consisting of poly dimethyl siloxane (PDMS), poly urethane acrylate (PUA), poly silicon (PS), poly vinyl alcohol (PVA), poly urethane (PU), and polyethylene glycol (PEG).

On another aspect, the present invention provides a vibration transmission interface component including a dry adhesive patch and a vibration layer attached to the opposite surface of the interlocking surface of the first or second layer not bonded to the microchannel structure layer.

The component may be a haptic interface component.

On another aspect, the present invention provides a virtual reality/augmented reality (VR/AR) tactile information implementation device including the vibration transmission interface component of claim 22.

BRIEF DESCRIPTION OF THE DRAWINGS

FIG. 1 shows a schematic diagram and cross-section of a vibration-resistant dry skin adhesive patch 1 of the present invention;

DETAILED DESCRIPTION OF THE INVENTION

Figure 2A:
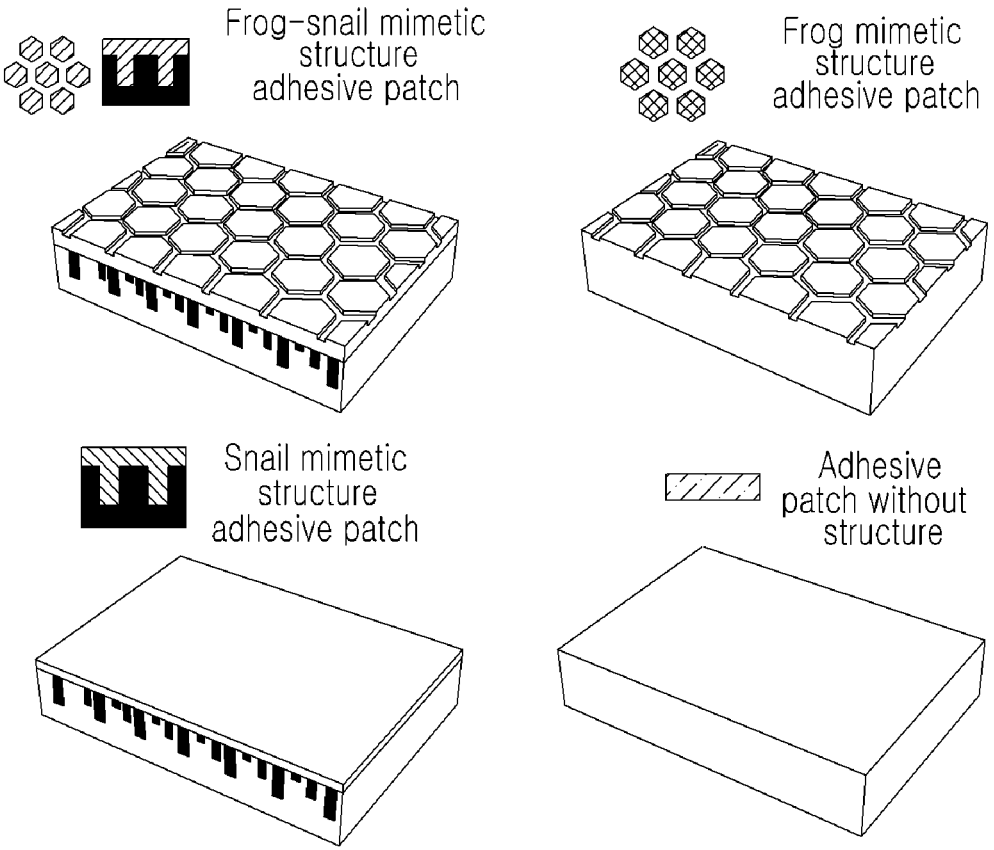
FIG. 2A shows each of the structure of the frog-snail mimetic structure adhesive patch, frog mimetic structure adhesive patch, snail mimetic structure adhesive patch, and adhesive patch without structure.

Hereinafter, embodiments of the present invention will be described in detail with reference to accompanying drawings. Since the present invention can be subject to various changes and modifications, the preferred embodiments are illustrated in the drawings and described in detail in the specification. However, such embodiments are not intended to limit the invention and it should be understood that the embodiment include all changes, equivalents, and substitutes within the spirit and scope of the invention. Throughout the drawings, like reference numerals refer to like components. In the accompanying drawings, the dimensions of the structures may be enlarged to show the invention more clearly.

The terminology used in this application is employed merely to describe specific embodiments and is not intended to limit the scope of the present invention. As used herein, the singular forms are intended to include the plural forms as well, unless the context clearly indicates otherwise. In this application, terms such as "include" or "have' are intended to indicate the presence of features, numbers, steps, operations, components, or combinations thereof as disclosed in the specification, but should be understood not to preclude the presence or possibility of one or more other features, numbers, steps, operations, components, or combinations thereof.

Unless otherwise defined herein, all terms including technical or scientific terms used herein have the same meanings as commonly understood by those skilled in the art to which the present invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The present invention is a vibration-resistant dry skin adhesive patch exhibiting high adhesive strength in moist and rough skin environments and vibration resistance, and simultaneously transmitting vibration applied to the patch to the skin without loss.

That is, the vibration-resistant dry skin adhesive patch achieves intimate contact with moist and rough skin through a surface adhesive layer that facilitates drainage via microchannel structures, while simultaneously minimizing skin irritation through enhanced breathability. Furthermore, the microstructure connected in an interlocking structure inside the patch reinforces surface adhesion and disperses physical stimuli such as vibrations, allowing the maintenance of high adhesive strength even under repetitive vibrations.

Figure 1:
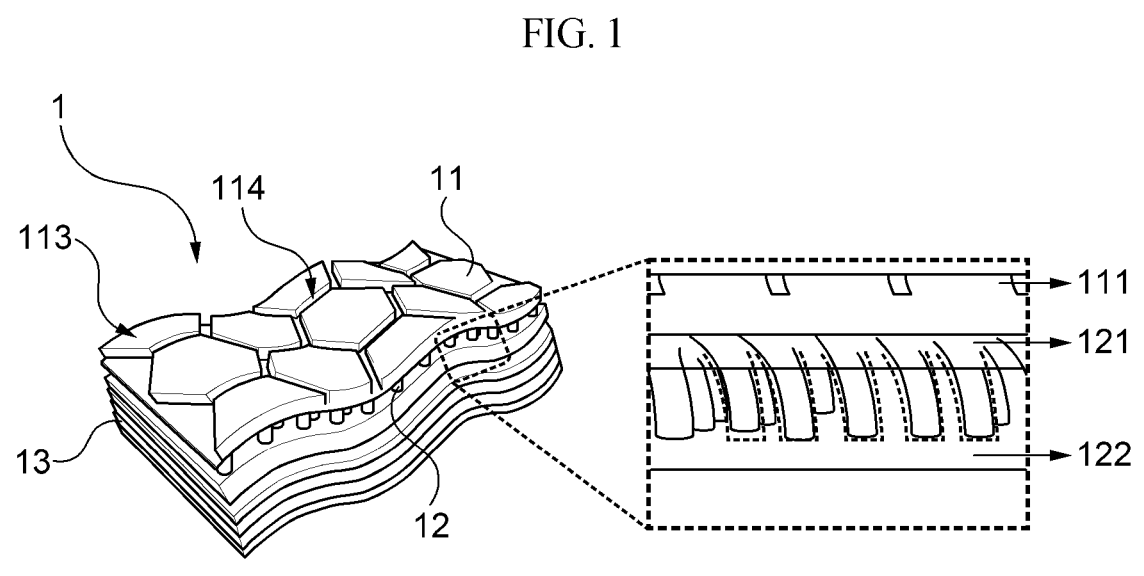

FIG. 1 shows a schematic diagram and cross-section of a vibration-resistant dry skin adhesive patch 1 of the present invention. The patch of the present invention includes a flexible first layer 121 based on a snail mimetic interlocking structure, featuring structures with either embossed or engraved patterns on one side; a flexible second layer 122 configured to engage with the embossed or engraved structures of the first layer, forming an interlocking coupling surface through the engagement; and a microchannel structure layer 111 stacked on the opposite surface of the interlocking coupling surface and formed based on frog mimetic microchannel structure to serve as a skin surface adhesive portion. The adhesive surface of the microchannel structure layer includes a plurality of embossed portions 113 with flat surfaces and microchannel grooves 114 between the embossed portions and is exposed to constitute a dry adhesive patch. A vibration transmission portion 13 utilizing a vibration generation device may be included.

The elastic layer, which includes the microchannel structure and embossed cylindrical structures 121, is represented in turquoise, while the elastic layer, which includes engraved cylindrical structures 122 connectable to the embossed cylindrical structures, is represented in semi-transparent black. The microchannel structure included in the skin surface adhesive portion is in contact with the skin surface, and moisture such as sweat generated on the skin passes through the channel structure for discharge, thereby regulating the moisture on the adhesive surface and inducing strong adhesive strength. Additionally, the microchannel structure, aided by protruding microstructures between channels, prevents continuous detachment propagation, thereby enhancing the peel strength of the adhesive patch. Furthermore, these microchannel structures allow air to escape through the channels, providing comfortable breathability and minimizing skin irritation on the adhesive surface. The microstructure connection portion involves almost no chemical bonding between layers, instead maintaining the connection between layers through an interlocking arrangement of cylindrical structures. Each layer in the interlocking arrangement is composed of elastomers with different degrees of elasticity, combining elastomers with low elasticity in the engraved structure and elastomers with high elasticity in the embossed structure. When the necessary force for detachment is applied from the opposite side of the skin, the elastomer of the engraved structure moves due to the force, and the frictional force on the interlocked surface causes the elastomer of the embossed structure with high elasticity to elongate. The interlocking microstructures evenly distributed across the entire surface of the adhesive patch disperse the stress concentrated on the fracture surface throughout the entire surface of the adhesive patch through the elongation of the embossed structure elastomer, enhancing surface adhesion. Furthermore, the dispersion of detachment energy generated by the elasticity of the microstructures enhances the vibration resistance of the adhesive patch by dispersing the vibrations repeatedly applied through the connected vibration generation device. Adhesion with chemically bonded point elasticity leads to a deterioration in adhesive performance due to the destruction of chemical bonds from repeated vibrations, whereas physical energy dispersion through elasticity maintains adhesive performance even under repetitive vibrations.

The completed vibration-resistant dry skin adhesive patch must have at least one microstructure connection portion based on an interlocking structure. The microstructure connection portion should involve an interaction that, upon applying stress inducing detachment, disperses the stress across the entire surface of the adhesive patch through the elongation of cylindrical structures, thereby enhancing the adhesive capability of the skin surface adhesive layer. As such interaction cannot occur unless minimal surface adhesion is ensured on the adhesive surface, the completed vibration-resistant dry skin adhesive patch of the present invention must have at least one microchannel structure on the skin surface adhesive portion.

It is composed of an elastic layer that includes the microchannel structure and embossed cylindrical structures and an elastic layer that includes engraved cylindrical structures connectable to the embossed cylindrical structures. Each layer may be made of various elastomers, including polymers such as PDMS, PUA, PEG, PS, PU, and PVA, as well as Dow Corning® Sylgard™, NuSil® brand medical-grade silicone, and Smooth-On Inc. The layers can be made of various elastomers, including commercial silicone materials such as Ecoflex™, and Dragon Skin™. The vibration generation device at the top is represented in yellow-brown color and constitutes the vibration transmission portion in FIG. 1. The vibration generation device may be produced in the form of an actuator based on various types of piezoelectric components and may be constructed by securing the vibration transmission portion on a surface without a structure of a black elastic solid layer and wrapping it with various elastomers as a finishing material to prevent damage to the entire adhesive patch. The vibration transmission portion may be selectively modified, reinforced, or removed based on the intended use of the skin adhesive patch, and, regardless of the presence of the vibration transmission portion, the strong adhesion to the skin is maintained by the interlocking microstructures. In this case, the interlocking structure is designed, modified, or improved to disperse various physical stimuli the may hinder the smooth adhesion of the adhesive patch.

Embodiment 1

To verify the adhesive strength of the frog-snail mimetic structure adhesive patch of the present invention, various adhesive patches with different structures were fabricated as comparative groups, and adhesive strength measurements were conducted for comparison.

In detail, the comparative group includes a frog mimetic structure adhesive patch with only a microchannel structure layer on the surface, a snail mimetic structure adhesive patch with only an interlocking structure inside, and an adhesive patch with no microstructure.

In the experiment, the adhesive target surface was measured for adhesion in both dry conditions and humid conditions with sweat.

Figure 2B:
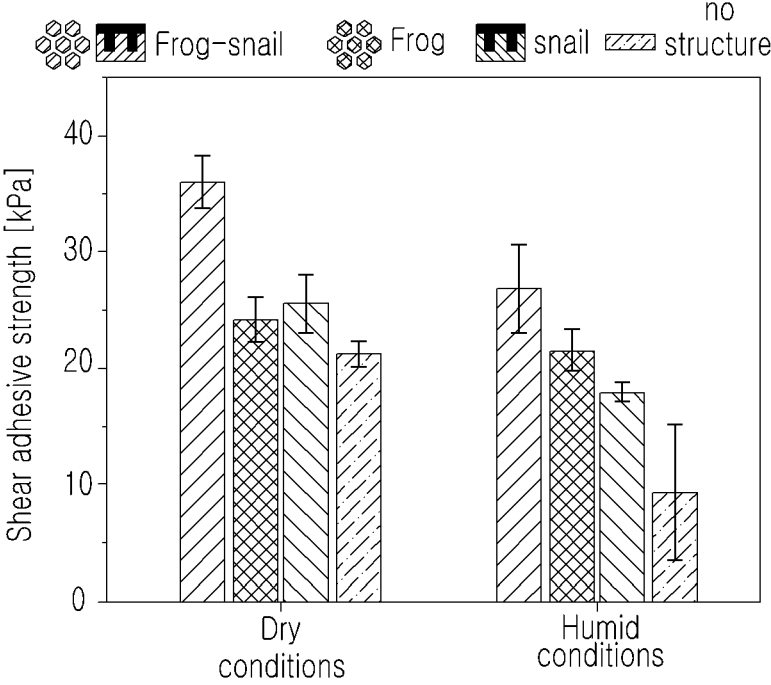
FIG. 2B shows superiority of the frog-snail mimetic structure adhesive patch according to the first embodiment of the present invention in adhesion as a comparison result with a comparative group.
Figure 2C:
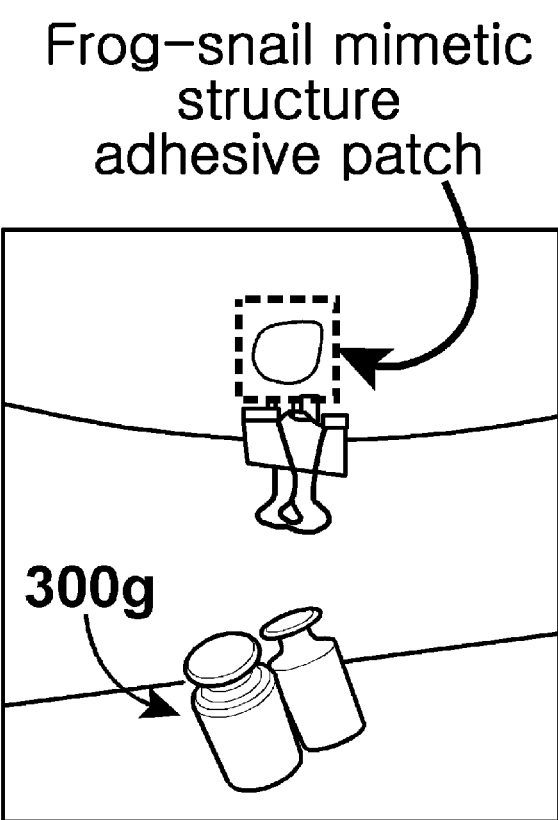
FIG. 2C shows a Photo of actual application of frog-snail mimetic structure adhesive patch.
Figure 3A:
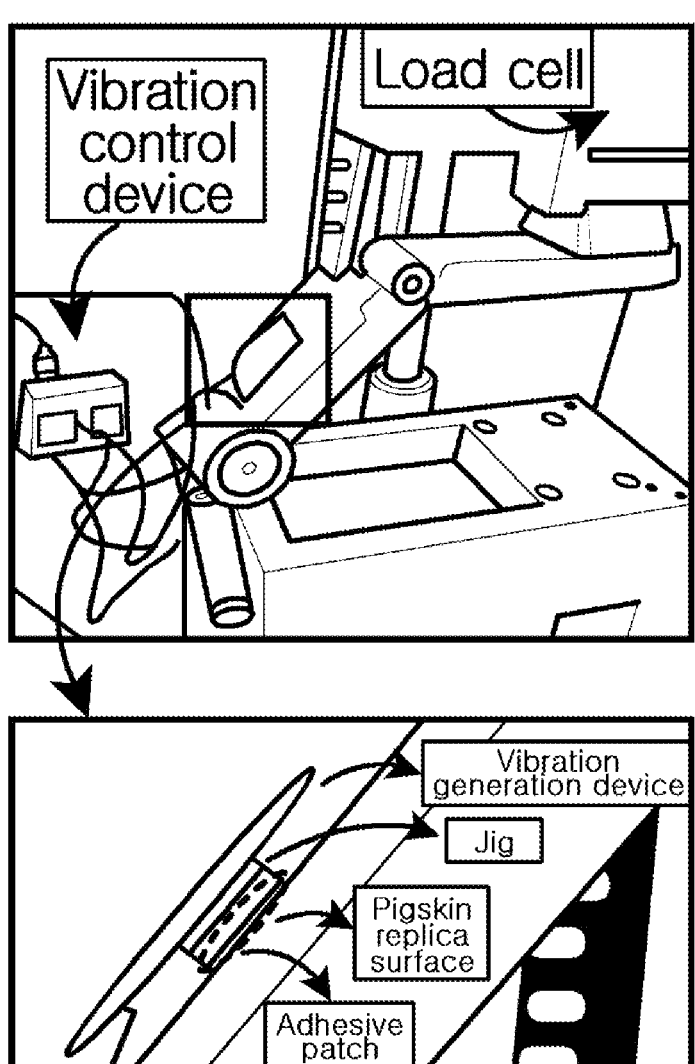
FIG. 3A shows the photo of the vibration control device.
Figure 3B:
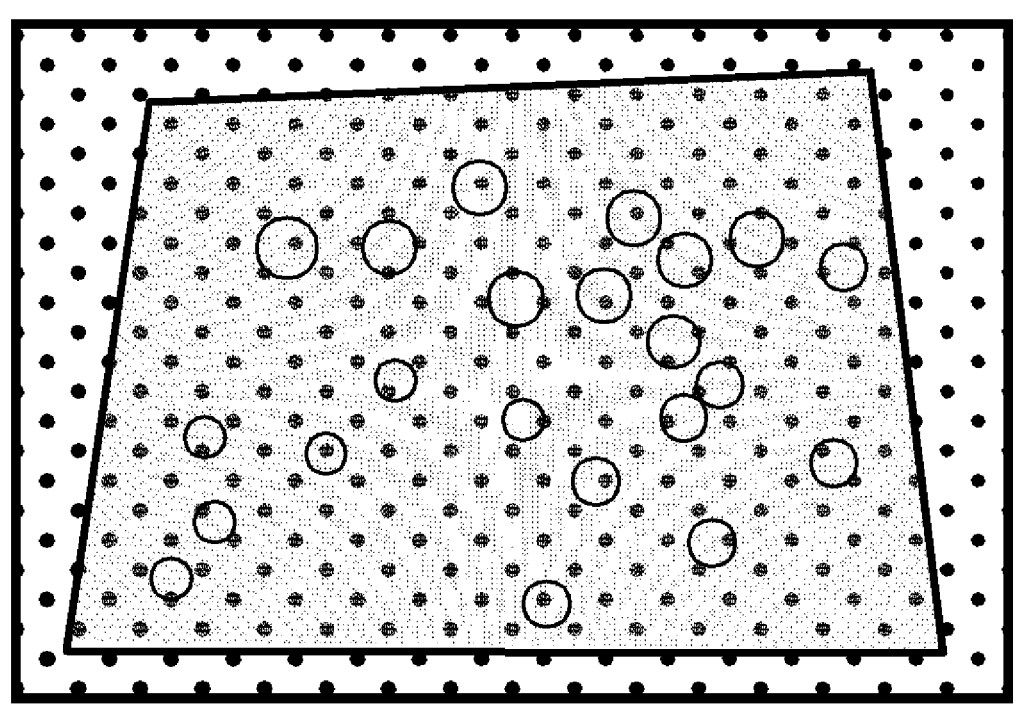
FIG. 3B shows Pigskin replica surface with sweat which is used in the Embodiments.
Figure 3C:
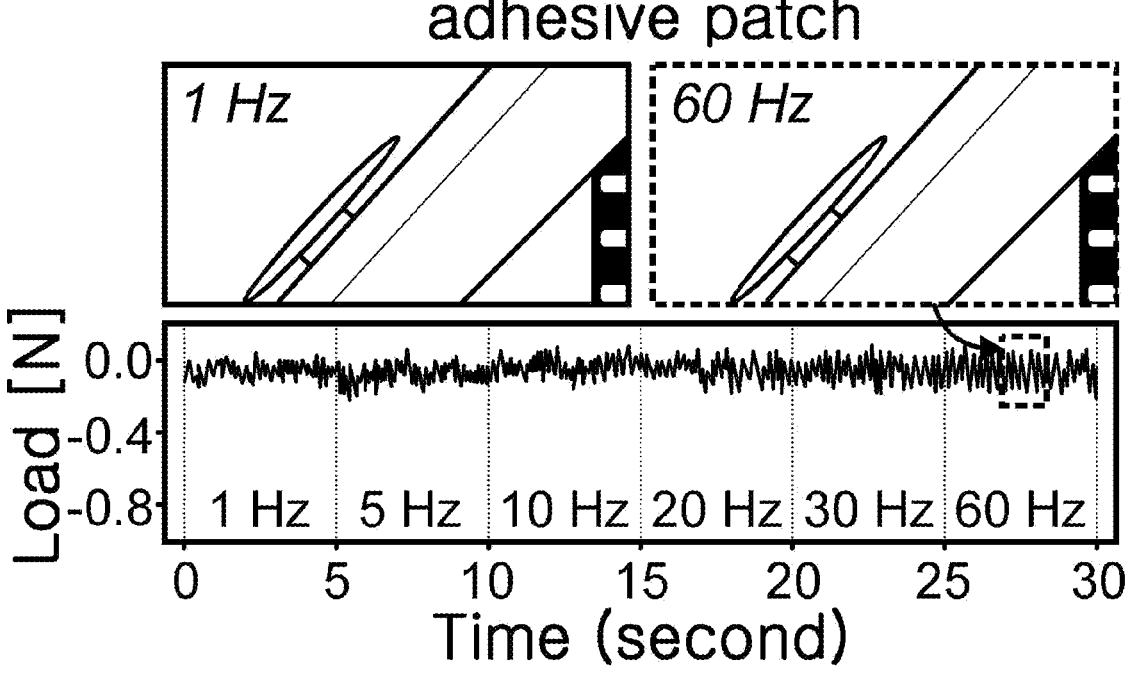
FIG. 3C, FIG. 3D, FIG. 3E, and FIG. 3F show superiority of the frog-snail mimetic structure adhesive patch according to the second embodiment of the present invention in vibration resistance as a comparison result with a comparative group.
Figure 3D:
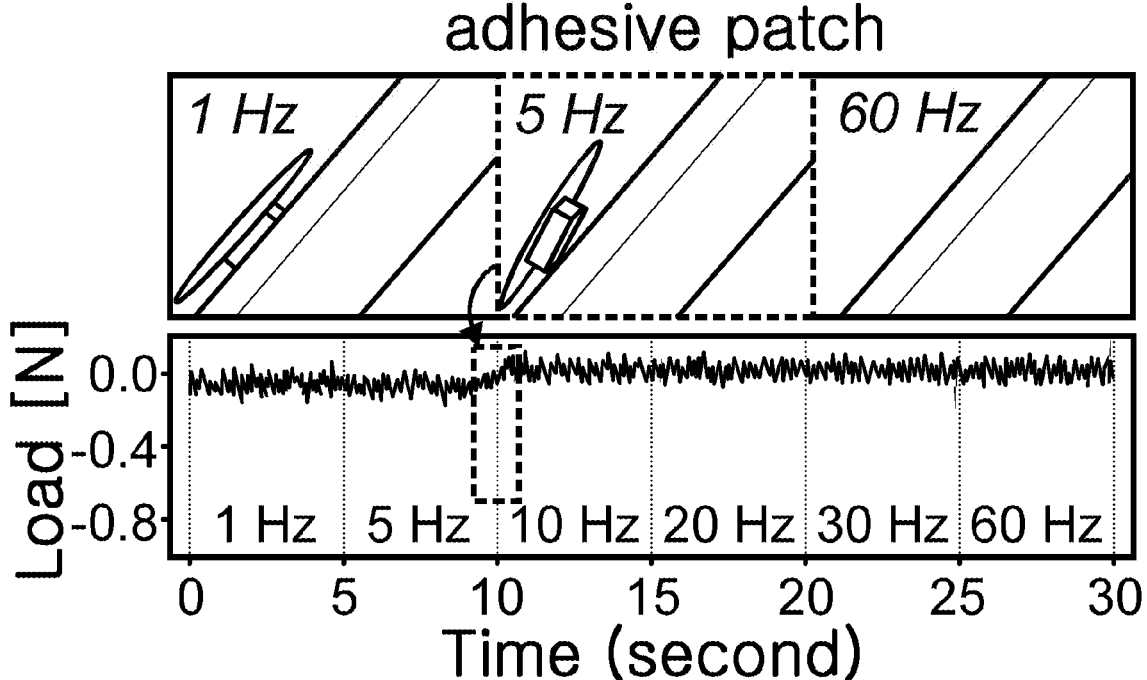
Figure 3E:
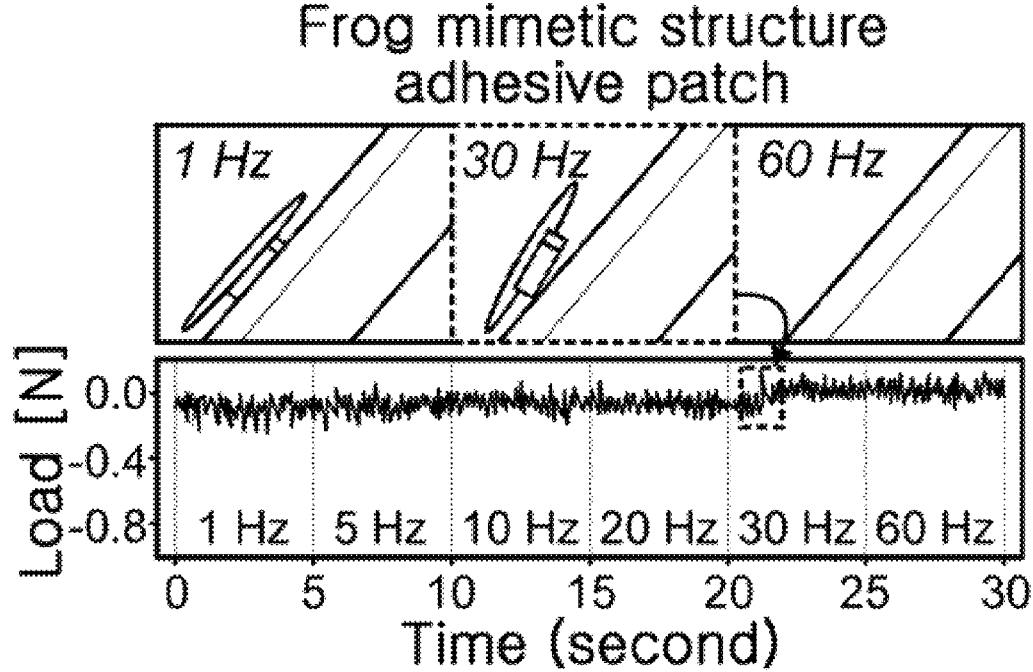
Figure 3F:
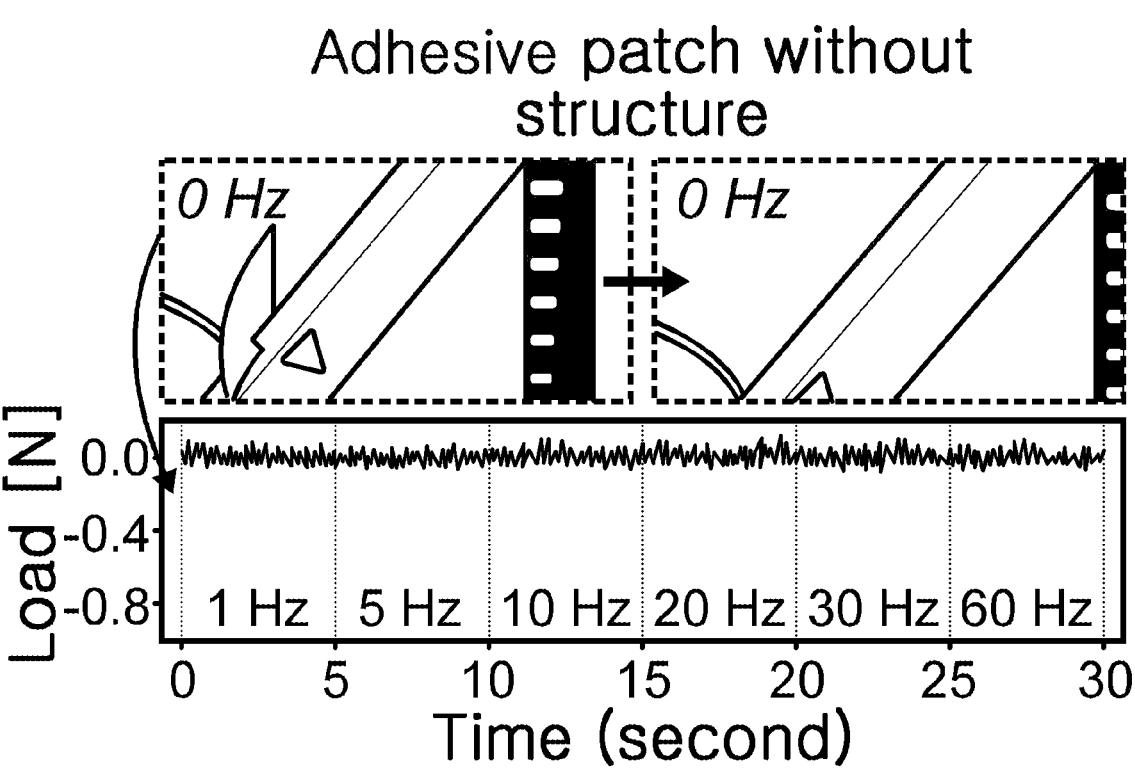

The experimental results showed that the frog-snail mimetic structure adhesive patch exhibited the highest adhesion in both dry and humid conditions (maximum adhesion in dry conditions ~36.0 kPa, maximum adhesion in humid conditions ~26.8 kPa). In dry conditions, the snail mimetic structure adhesive patch, enhanced by the interlocking structure, exhibited higher adhesion compared to the other two comparative groups; however, in humid conditions, the frog mimetic structure adhesive patch with microchannel structures showed even higher adhesion. Especially in humid conditions, the adhesion strength of the snail mimetic structure adhesive patch significantly decreased compared to dry conditions, attributed to the difficulty in achieving elongation of the point-elastic microstructures without ensuring surface adhesion. Based on these experimental results, it can be confirmed that the frog mimetic structure and snail mimetic structure mutually complementarily increase adhesion strength. Furthermore, it was confirmed that the frog-snail mimetic structure adhesive patch of the present invention withstood a weight of 300 g while adhered to human skin. The results are shown in FIG. 2.

Embodiment 2

To verify the variation resistance of the frog-snail mimetic structure adhesive patch of the present invention, various adhesive patches with different structures were fabricated as comparative groups, and vibration resistance measurement experiments were conducted for comparison. In this case, the adherend surface is a pigskin replica surface simulating a humid state with sweat. The vibration generator, adhesive patch, and pigskin replica surface were connected using a jig to conduct the experiments. The frequency of the vibrations applied by the connected vibration control device was adjusted, and a load cell was used to measure the detachment time of the adhesive patch.

The experimental results confirmed that the frog-snail mimetic structure adhesive patch maintained adhesion even at a high frequency of 60 Hz. On the other hand, the frog mimetic structure adhesive patch with low vibration resistance failed to maintain adhesive performance when subjected to vibrations at a frequency of 30 Hz. The snail mimetic structure adhesive patch failed to secure minimal surface adhesion on the sweaty adhesive surface and detached when subjected to vibrations at a frequency of 5 Hz. Similarly, the adhesive patch with no specific structure failed to secure minimal surface adhesion, and adhesion to the surface did not occur even without applying vibrations.

Embodiment 3

Figure 4:
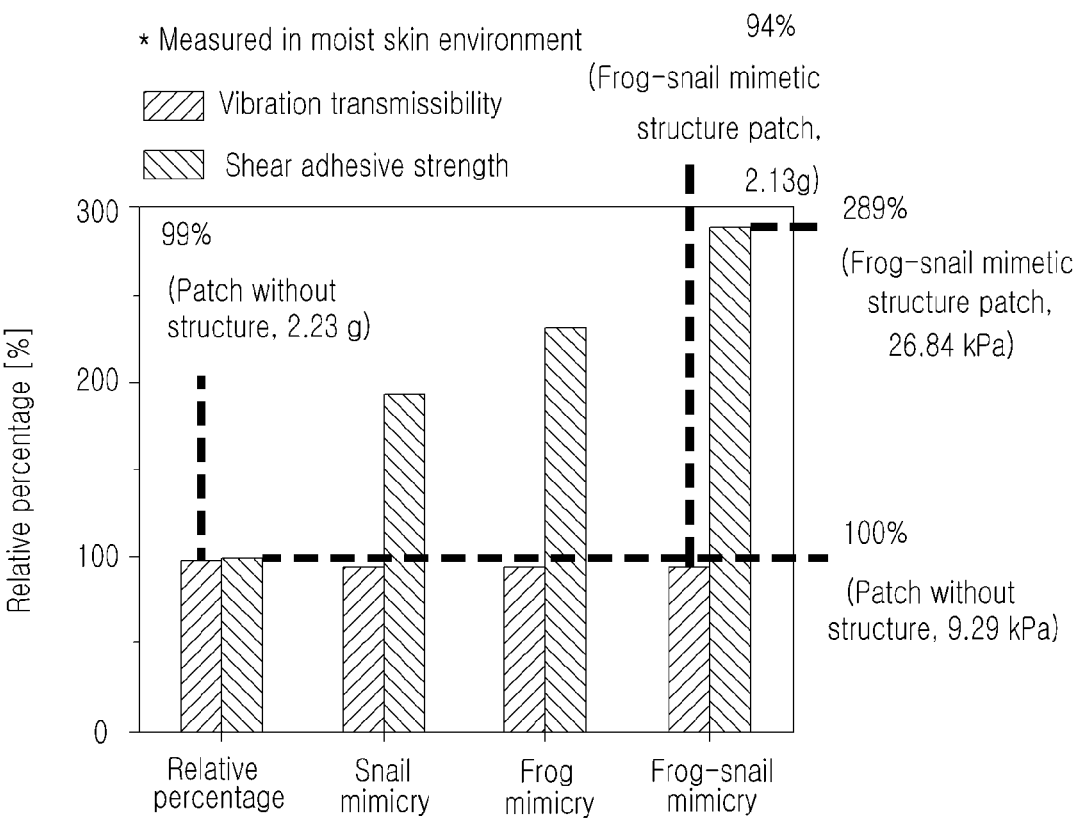
FIG. 4 is graph representing the result of the third embodiment.

It was verified whether the frog-snail mimetic structure adhesive patch has high adhesion while simultaneously transmitting vibration applied to the patch to the skin without loss. The acceleration of the applied vibration in the experiment was 2.26 g, and the vibration transmissibility was calculated by measuring the acceleration of the vibration transmitted through the adhesive patch. The frog-snail mimetic structure adhesive patch transmits 94% of the vibration, while the adhesive patch without any structure transmits 99% of the vibration. However, it can be confirmed that the frog-snail mimetic structure adhesive patch shows a 289% increase in adhesion compared to the adhesive patch without any structure. The results of this experiment demonstrate that the adhesive patch of the present invention not only achieves a significant improvement in adhesion but also transmits all vibrations without loss. The results are shown in FIG. 4.

Embodiment 4

Figure 5:
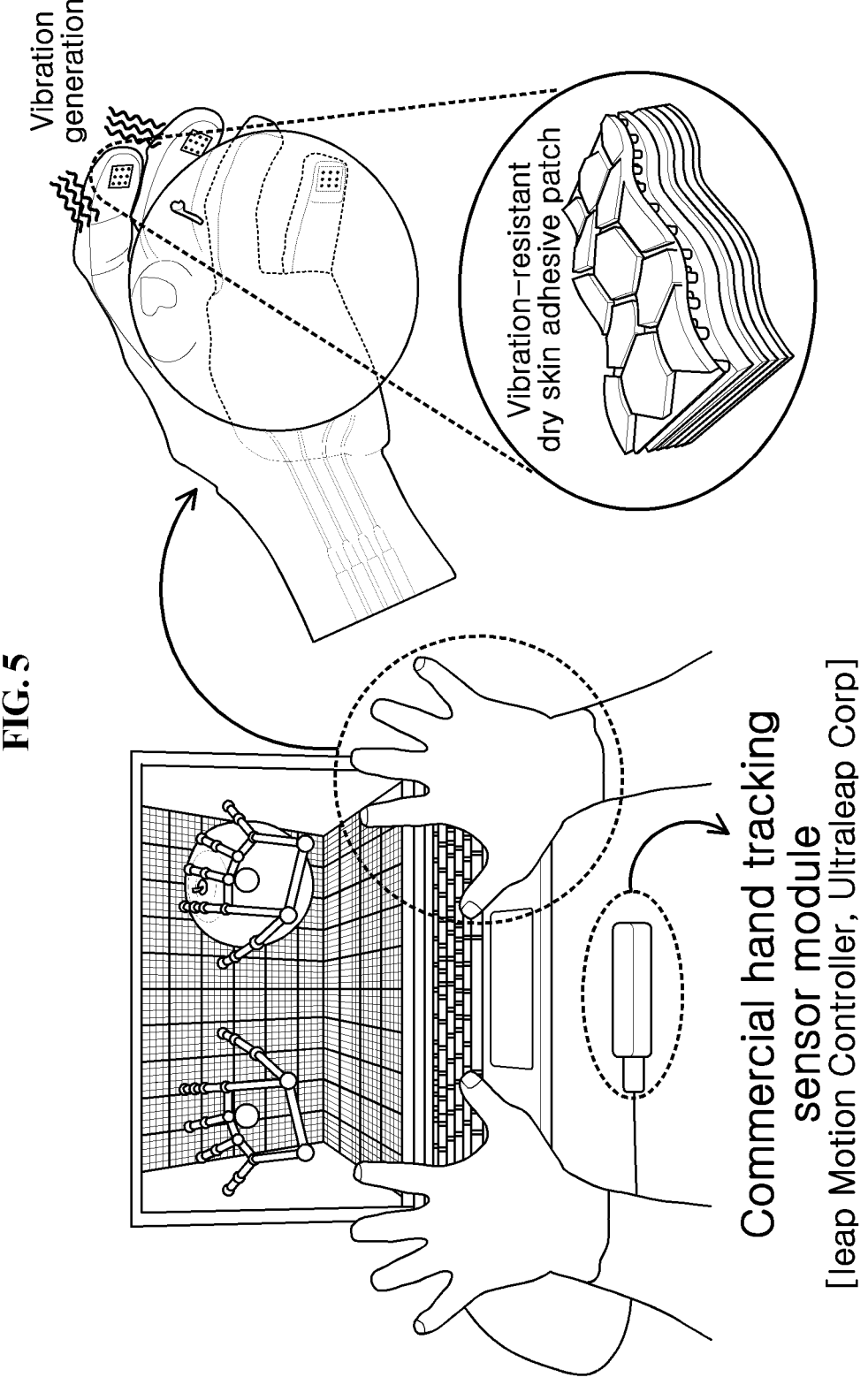
FIG. 5 is a schematic diagram illustrating an exemplary application of the vibration-resistant dry skin adhesive patch of the present invention in an electronic device interface technology.

FIG. 5 is a schematic diagram illustrating an exemplary application of the vibration-resistant dry skin adhesive patch of the present invention in an electronic device interface technology, particularly as a tactile information implementation device in VR/AR. The diagram demonstrates the process of implementing the hand in a virtual world by tracking the movement of a person's hand in the real world and, when grasping objects in the virtual world, applying vibrations to the real-world hand to convey tactile information. In this process, the adhesive patch of the present invention, which is connected by interlocking structures and possesses strong vibration resistance, maintains adhesion to the skin even under repetitive vibrations. This adhesive patch also has a high vibration transmissibility, allowing precise tactile stimuli to be transmitted to the hand. Furthermore, the adhesive patch of the present invention is designed to be suitable for sweaty and rough skin environments, ensuring that it does not detach from the skin even when sweat is generated.

The present invention has high adhesion on wet and rough skin surfaces and can maintain adhesion even in a vibrating environment. The skin adhesive patch of the present invention can overcome and address various limitations associated with chemical adhesive-based skin adhesives and conventional dry adhesives that have been developed so far. Specifically, the skin adhesive patch of the present invention can overcome the limitations of conventional skin adhesives in adhering closely to the skin in rough and moist dynamic biological environments by utilizing the drainage capability provided by microchannel structures, while also offering comfortable breathability to minimize skin irritation. In addition, the present invention provides a design method that goes beyond the limitations of dry adhesive technology that relied solely on surface structures by amplifying the surface adhesion through microstructures interlocked within the patch. Furthermore, the present invention provides an adhesive mechanism that disperses physical stimuli, such as vibrations applied to the adhesive patch, through microstructures inside the patch, maintaining high adhesion even under repetitive vibrations. These effects of the skin adhesive patch of the present invention enables the development of new design and manufacturing methods for interfaces for VR/AR haptic devices that are frequently exposed to repetitive vibrations and are used in sweaty and rough skin environments.

The above description of the present invention is for illustrative purposes only, and it will be understood by those skilled in the art that various modifications and changes may be made thereto without departing from the spirit and scope of the invention. Therefore, it should be understood that the embodiments described above are exemplary and not limited in all respects. For example, each component described as a single type may be implemented in a distributed manner, and similarly, components described as distributed may be implemented in a combined form.

The scope of the present invention is determined by the appended claims rather than the specification above, and any modifications or variations derived from the meaning and scope of the claims and their equivalence should be interpreted as included the scope of the claims of the present invention.

What is claimed is:

1. A dry adhesive patch comprising:
a first layer, flexible and having a structure with embossed or engraved structures on one surface;
a second layer, flexible and comprising an interlocking coupling surface formed to engage with the embossed or engraved structures of the first layer; and
a microchannel structure layer stacked on the surface of the second layer opposite the interlocking coupling surface,
wherein the microchannel structure layer comprises an exposed adhesive surface comprising a plurality of embossed portions having a flat surface and microchannel grooves between the embossed portions.

2. The dry adhesive patch of claim 1, wherein the dry adhesive patch is a vibration-resistant patch.

3. The dry adhesive patch of claim 2, wherein a vibration frequency dampened by the dry adhesive patch is equal to or higher than 30 Hz.

4. The dry adhesive patch of claim 3, wherein the dry adhesive patch has a vibration transmissibility equal to or greater than 99%.

5. The dry adhesive patch of claim 1, wherein the dry adhesive patch is for use on a moist skin surface.

6. The dry adhesive patch of claim 1, wherein the second layer comprises an embossed structure, and the first layer comprises an engraved structure interlocking with the embossed structure of the second layer.

7. The dry adhesive patch of claim 6, wherein the first layer and the second layer have different deformation rates in response to stress.

8. The dry adhesive patch of claim 7, wherein the second layer has a higher deformation rate in response to stress compared to the first layer.

9. The dry adhesive patch of claim 7, wherein the second layer is made of a more flexible material compared to the first layer.

10. The dry adhesive patch of claim 7, wherein the embossed portions of the microchannel structure layer are hexagonal in plane and form hexagonal columns.

11. The dry adhesive patch of claim 10, wherein the microchannel grooves have a width configured to allow capillary action by moisture between an adhered surface of the adhesive patch and the microchannels.

12. The dry adhesive patch of claim 11, wherein the width of the microchannel grooves ranges from 1 nm to 1000 μm.

13. The dry adhesive patch of claim 12, further comprising a hydrogel layer on at least part of a base surface of the microchannel grooves.

14. The dry adhesive patch of claim 13, wherein the hydrogel layer has a height lower than the height of the embossed portions from the base surface of the microchannel grooves.

15. The dry adhesive patch of claim 14, wherein the microchannel structure layer comprises at least one of natural rubber, nitrile rubber, acrylonitrile-butadiene rubber, styrene-butadiene rubber, chloroprene rubber, butyl rubber, isoprene-isobutylene rubber, ethylene propylene rubber, chlorosulphonated polyethylene rubber, acrylic rubber, fluoro rubber, polysulfide rubber, silicone rubber, butadiene rubber, isoprene rubber, urethane rubber, polyurethane, polyolefin thermoplastic elastomer (TPE), polystyrene TPE, polyvinyl chloride TPE, polyester TPE, polyurethane TPE, polyamide TPE, polyethylene terephthalate (PET), polydimethylsiloxane (PDMS), polyurethane acrylate, polyethylene naphthalate (PEN), and mixtures thereof.

16. The dry adhesive patch of claim 1, wherein the interlocking coupling surface comprises a chemical adhesive.

17. The dry adhesive patch of claim 1, wherein the embossed or engraved structures on the first layer have a diameter of 1 pm to $10^2$ pm.

18. The dry adhesive patch of claim 1, wherein the first and the second layers are made of elastomeric or viscoelastic solid or viscoelastic fluid.

19. The dry adhesive patch of claim 1, wherein the first and second layers are made of at least one selected from the group consisting of poly dimethyl siloxane (PDMS), poly urethane acrylate (PUA), poly silicon (PS), poly vinyl alcohol (PVA), poly urethane (PU), and polyethylene glycol (PEG).

20. A vibration transmission interface component comprising:
a dry adhesive patch of claim 1; and
a vibration layer attached to the other surface of the first layer opposite the surface on which the structure with embossed or engraved structures is formed.

21. The vibration transmission interface component of claim 20, wherein the component is a haptic interface component.

22. A virtual reality/augmented reality (VR/AR) tactile information implementation device comprising the vibration transmission interface component of claim 21.

* * * * *